(12) United States Patent
Holstein

(10) Patent No.: US 9,072,625 B2
(45) Date of Patent: Jul. 7, 2015

(54) EASY ACCESS BANDAGES, PACKAGING, AND SYSTEMS FOR APPLICATION

(71) Applicant: Michael Holstein, Clearwater, FL (US)

(72) Inventor: Michael Holstein, Clearwater, FL (US)

(73) Assignee: GENUINE FIRST AID INTERNATIONAL, LTD., Road Town, Tortola (VG)

(*) Notice: Subject to any disclaimer, the term of this patent is extended or adjusted under 35 U.S.C. 154(b) by 68 days.

(21) Appl. No.: 13/666,659

(22) Filed: Nov. 1, 2012

(65) Prior Publication Data

US 2014/0116907 A1     May 1, 2014

(51) Int. Cl.
*A61F 13/00*     (2006.01)

(52) U.S. Cl.
CPC .................................. *A61F 13/0008* (2013.01)

(58) Field of Classification Search
CPC ........... A61F 13/0008; A61F 13/00085; A61F 13/00072; A61F 13/00076; A61F 15/002; A61F 15/001; A61F 15/005
USPC .......................... 206/441, 440; 602/54, 57, 41
See application file for complete search history.

(56) References Cited

U.S. PATENT DOCUMENTS

| | | | |
|---|---|---|---|
| 1,262,963 A | 4/1918 | McCrea | |
| 1,487,014 A | 3/1924 | Davis | |
| 1,564,152 A | 12/1925 | Thomson | |
| 2,330,457 A | 9/1943 | Tremblett | |
| 2,523,804 A | 9/1950 | Albro | |
| 2,564,712 A | 8/1951 | Muros et al. | |
| 2,889,039 A * | 6/1959 | Schladermundt et al. | 206/441 |
| 2,897,961 A * | 8/1959 | Bush | 206/441 |
| 2,946,435 A * | 7/1960 | Schladermundt et al. | 206/441 |
| 2,969,145 A * | 1/1961 | Hannauer, Jr. | 206/441 |
| 3,217,967 A | 11/1965 | Jackson | |
| 3,231,076 A | 1/1966 | Freiman | |
| 3,349,454 A | 10/1967 | Thomson | |
| 3,389,784 A | 6/1968 | Hendricks et al. | |
| 3,899,077 A * | 8/1975 | Spiegelberg | 206/441 |
| 4,011,945 A | 3/1977 | Bourne et al. | |
| 4,194,624 A | 3/1980 | Spiegelberg | |
| 4,201,029 A | 5/1980 | Lerner et al. | |
| 4,231,357 A | 11/1980 | Hessner | |
| 4,235,337 A * | 11/1980 | Dotta | 206/441 |

(Continued)

FOREIGN PATENT DOCUMENTS

| | | |
|---|---|---|
| DE | 9400932 U1 | 5/1994 |
| EP | 0948949 | 10/1999 |

(Continued)

OTHER PUBLICATIONS

Genuine First Aid 2009 First Aid Catalog.

(Continued)

*Primary Examiner* — Steven A. Reynolds
(74) *Attorney, Agent, or Firm* — Wilson Sonsini Goodrich & Rosati

(57) ABSTRACT

Provided are a bandage wrappers and bandage application systems with a first wrapper element and a second wrapper element; whereby the first wrapper element and the second wrapper element at least partially enclose an individual bandage and are separable in contact to completely enclose the bandage such that when the first and second wrapper elements are pulled in opposite directions the first and second elements separate to partially expose the bandage in a ready-to-apply state.

19 Claims, 6 Drawing Sheets

(56) References Cited

U.S. PATENT DOCUMENTS

| | | | |
|---|---|---|---|
| 4,394,904 A | 7/1983 | Larimore | |
| 4,418,822 A * | 12/1983 | Dotta | 206/441 |
| 4,502,596 A | 3/1985 | Saetre et al. | |
| 4,549,653 A | 10/1985 | Lauritzen | |
| 4,561,435 A | 12/1985 | McKnight et al. | |
| 4,563,832 A | 1/1986 | Drebot | |
| 4,564,108 A | 1/1986 | Widlund et al. | |
| 4,616,644 A | 10/1986 | Saferstein et al. | |
| 4,807,753 A | 2/1989 | Goldstein | |
| 4,846,164 A | 7/1989 | Martz | |
| 4,858,604 A * | 8/1989 | Konishi | 602/57 |
| 4,867,821 A | 9/1989 | Morgan | |
| 4,887,611 A | 12/1989 | Rudiger et al. | |
| 4,917,688 A | 4/1990 | Nelson et al. | |
| 4,972,657 A | 11/1990 | McKee | |
| 5,117,981 A | 6/1992 | Crawford et al. | |
| 5,160,328 A | 11/1992 | Cartmell et al. | |
| 5,244,523 A | 9/1993 | Tollini | |
| 5,271,522 A | 12/1993 | Ko et al. | |
| 5,275,284 A * | 1/1994 | Onotsky | 206/441 |
| 5,397,297 A * | 3/1995 | Hunter | 602/54 |
| 5,511,689 A | 4/1996 | Frank | |
| 5,533,962 A | 7/1996 | Peterman et al. | |
| 5,593,395 A | 1/1997 | Martz | |
| 5,685,833 A | 11/1997 | Turngren | |
| 5,733,626 A | 3/1998 | Middleton | |
| 5,843,011 A | 12/1998 | Lucas | |
| 5,848,700 A | 12/1998 | Horn | |
| 5,931,304 A | 8/1999 | Hammond | |
| 6,010,002 A * | 1/2000 | Petterson | 206/441 |
| 6,016,915 A | 1/2000 | Almond | |
| 6,018,092 A | 1/2000 | Dunshee | |
| 6,050,413 A | 4/2000 | Benedetti | |
| 6,053,318 A * | 4/2000 | Petterson | 206/440 |
| 6,076,700 A | 6/2000 | Manges | |
| 6,124,522 A | 9/2000 | Schroeder | |
| 6,140,549 A * | 10/2000 | Pompei, Jr. | 602/57 |
| 6,299,018 B1 | 10/2001 | Kimbrell | |
| 6,369,289 B1 | 4/2002 | Orr | |
| 6,719,137 B2 * | 4/2004 | Dotta | 206/441 |
| 6,855,861 B2 * | 2/2005 | Dotta | 602/57 |
| 7,045,144 B2 | 5/2006 | Schunk et al. | |
| 7,495,146 B2 | 2/2009 | Crisp | |
| 7,659,439 B2 * | 2/2010 | Grossman | 602/57 |
| 7,854,322 B2 * | 12/2010 | Dotta | 206/441 |
| 7,866,537 B1 * | 1/2011 | Duhon | 229/87.05 |
| 7,994,382 B2 | 8/2011 | Bartholomaeus | |
| 8,052,009 B2 | 11/2011 | Blum et al. | |
| 8,167,130 B2 | 5/2012 | Holstein | |
| 8,302,775 B2 | 11/2012 | Holstein | |
| 8,336,712 B2 | 12/2012 | Holstein | |
| 8,511,470 B2 * | 8/2013 | Grossman | 206/441 |
| 8,522,976 B2 | 9/2013 | Holstein | |
| 8,770,406 B2 | 7/2014 | Holstein | |
| 2002/0008047 A1 | 1/2002 | Hammond | |
| 2002/0064619 A1 | 5/2002 | Schroeder | |
| 2002/0104774 A1 | 8/2002 | Hammond | |
| 2002/0162847 A1 | 11/2002 | Roy | |
| 2002/0170841 A1 | 11/2002 | Persson | |
| 2002/0195367 A1 * | 12/2002 | Dotta | 206/440 |
| 2003/0009989 A1 | 1/2003 | Knoerzer et al. | |
| 2003/0075470 A1 | 4/2003 | Cameron et al. | |
| 2003/0199800 A1 | 10/2003 | Levin | |
| 2003/0204158 A1 | 10/2003 | Johnson et al. | |
| 2004/0002676 A1 | 1/2004 | Siegwart et al. | |
| 2004/0004014 A1 | 1/2004 | Grossman | |
| 2004/0232013 A1 | 11/2004 | Renhed | |
| 2004/0256283 A1 | 12/2004 | Jasper et al. | |
| 2005/0017059 A1 | 1/2005 | Salani et al. | |
| 2005/0038369 A1 | 2/2005 | Gregory et al. | |
| 2005/0065492 A1 | 3/2005 | Cole et al. | |
| 2005/0256439 A1 | 11/2005 | Grossman | |
| 2006/0015053 A1 | 1/2006 | Crisp | |
| 2006/0148352 A1 | 7/2006 | Munro et al. | |
| 2006/0151347 A1 | 7/2006 | Grossman | |
| 2006/0154540 A1 | 7/2006 | Hilfenhaus et al. | |
| 2006/0289329 A1 | 12/2006 | Miller | |
| 2007/0010775 A1 | 1/2007 | Lutri | |
| 2007/0131577 A1 | 6/2007 | Call | |
| 2007/0175931 A1 | 8/2007 | Leoncavallo et al. | |
| 2007/0191753 A1 | 8/2007 | Wendorf | |
| 2007/0272575 A1 | 11/2007 | Dickmann | |
| 2007/0282237 A1 | 12/2007 | Munro et al. | |
| 2008/0027366 A1 | 1/2008 | Da Silva | |
| 2008/0111454 A1 | 5/2008 | Spoljaric | |
| 2008/0190799 A1 | 8/2008 | Dotta | |
| 2008/0274146 A1 | 11/2008 | Bartholomaus et al. | |
| 2008/0283433 A1 | 11/2008 | Primer | |
| 2009/0120826 A1 | 5/2009 | Spoljaric | |
| 2009/0261010 A1 | 10/2009 | Grossman | |
| 2009/0308764 A1 | 12/2009 | Lee et al. | |
| 2010/0106107 A1 | 4/2010 | Nash et al. | |
| 2010/0222731 A1 | 9/2010 | Gajiwala | |
| 2010/0252472 A1 | 10/2010 | Law et al. | |
| 2010/0270324 A1 | 10/2010 | Blum et al. | |
| 2010/0276323 A1 | 11/2010 | Grossman | |
| 2012/0205275 A1 | 8/2012 | Arnett | |
| 2012/0292216 A1 | 11/2012 | Holstein | |
| 2012/0292217 A1 * | 11/2012 | Grossman | 206/441 |
| 2012/0318706 A1 | 12/2012 | Holstein | |
| 2013/0175193 A1 | 7/2013 | Holstein | |
| 2013/0256171 A1 * | 10/2013 | Kerdemelidis et al. | 206/441 |

FOREIGN PATENT DOCUMENTS

| | | |
|---|---|---|
| EP | 1222908 | 7/2002 |
| GB | 2018228 | 10/1979 |
| GB | 2395342 | 5/2004 |
| WO | WO2004/000688 | 12/2003 |
| WO | WO2005/062996 | 7/2005 |
| WO | WO2006/78200 | 7/2006 |
| WO | WO2006/078201 | 7/2006 |
| WO | WO2010/089090 | 8/2010 |
| WO | WO2011/011450 | 1/2011 |
| WO | WO2012/158569 | 11/2012 |
| WO | WO2013/103849 | 7/2013 |

OTHER PUBLICATIONS

Genuine First Aid 2009 Frequently Asked Questions http://www.genuinefirstaid.com/faqs.htm.
PCT/US2010/042651 International Preliminary Report on Patentability and Written Opinion dated Jan. 24, 2012.
PCT/US2010/042651 Search Report and Written Opinion mailed Feb. 28, 2011.
PCT/US2012/037659 International Preliminary Report on Patentability dated Nov. 19, 2013.
PCT/US2012/037659 International Search Report dated Dec. 14, 2012.
PCT/US2013/020325 International Preliminary Report on Patentability dated Jul. 8, 2014.
PCT/US2013/020325 International Search Report dated Apr. 29, 2013.
PCT/US2013/066682 International Search Report and Written Opinion dated Mar. 3, 2014.
Press Release: Genuine First Aid Releases New Life Saving System—Easy Access Pockets dated Oct. 21, 2009, http://www.24-7pressrelease.com/press-release/genuine-first-aid-releases-new-life-saving-system-easy-access-pockets-121155.php.
U.S. Appl. No. 12/509,321 Office Action dated Jun. 10, 2011.
U.S. Appl. No. 12/509,321 Office Action dated Oct. 12, 2011.
U.S. Appl. No. 13/109,908 Office Action dated Apr. 6, 2012.
U.S. Appl. No. 13/109,908 Office Action dated Jul. 20, 2012.
U.S. Appl. No. 13/594,601 Office Action dated Jul. 3, 2013.
U.S. Appl. No. 13/653,092 Office Action dated Oct. 25, 2013.
U.S. Appl. No. 13/344,487 Office Action dated Jan. 8, 2013.

* cited by examiner

Front Side           Back Side
(Non-Adhesive Surface)  (Adhesive Surface)

EASY ACCESS BANDAGES, PACKAGING, AND SYSTEMS FOR APPLICATION

BACKGROUND OF THE INVENTION

When injuries occur, the wound must be covered as soon as possible to prevent bacteria from entering our body and causing further harm through infection. One of the most troublesome issues in dealing with injuries is the possibility of an infection or secondary infection. Infections that are caused by bacteria entering the wound at any time after the initial injuring invent are identified as secondary infections. Even if the original injury already caused an infection, harm caused by secondary infections can be avoided through proper cleaning and rapid application of bandages to cover the wound. According to the World Health Organization (WHO), bandages provide not only a moist environment to promote skin cell recovery but also serve to reduce instances of infection by outside bacteria.

Bandages are the most widely used medical items for covering wounds such as punctures, scrapes, scratches, or cuts in order to prevent infection by outside bacteria. Of course, if the bandages themselves contain bacteria, the risk of a secondary infection is increased. For example, if the person handling the bandage introduces bacteria to the bandage before application to the wound, the chances of secondary infection is also increased. Traditional bandages include packaging requiring extensive manipulation, using two hands, to remove before the bandage can be applied.

SUMMARY OF THE INVENTION

Some existing bandage application systems require a bulky dispenser unit, which creates additional cost for consumers. Even where bandages are packaged for speedy application, a dispenser unit is traditionally required to present and hold bandages as they are dispensed. Other bandage application systems require a consumer to rip and tear the packaging apart to gain access to an adhesive bandage, which is slow and inconvenient. Advantages of the systems, packaging, and wrappers described herein include, but are not limited to, allowing rapid access to a sterile bandage, with one hand and in a ready-to-apply state, without the need for a separate dispenser unit.

In one aspect, disclosed herein are bandage application systems comprising: an individual sterile adhesive bandage; a first wrapper element; and a second wrapper element; whereby the first wrapper element and the second wrapper element at least partially enclose the bandage and are separably in contact to completely enclose the bandage such that when the first and second wrapper elements are pulled in opposite directions the first and second elements separate to partially expose the bandage in a ready-to-apply state. In some embodiments, the first and second wrapper elements each comprise two parallel sheets sealed on three of four sides. In some embodiments, the bandage, when in a ready-to-apply state, is characterized by having at least one exposed adhesive area in a condition to adhere to skin. In some embodiments, the first and second wrapper elements are each printed to indicate an appropriate grip area. In some embodiments, the first and second wrapper elements are printed with bandage application instructions. In some embodiments, the first and second wrapper elements are separably in contact via a perforated, scored, or overlapping region. In some embodiments, upon separation of the first and second wrapper elements, the partially exposed bandage remains associated with either the first or the second wrapper element. In some embodiments, separation of the first and second wrapper elements does not require ripping or tearing of either the first or the second wrapper element. In some embodiments, the bandage comprises: a backing; at least one absorbent region; at least one adhesive region, wherein adhesive is applied to the backing; and a protection paper overlaying each adhesive region. In further embodiments, upon separation of the first and second wrapper elements, at least one protection paper remains associated with either the first or the second wrapper element, thereby exposing the adhesive. In some embodiments, the bandage is a strip bandage about 76 mm long and about 25 mm wide. In some embodiments, the bandage is a strip bandage about 76 mm long and about 19 mm wide. In some embodiments, the bandage is a strip bandage about 40 mm long and about 10 mm wide. In some embodiments, the bandage is a knuckle bandage about 76 mm long and about 38 mm wide. In some embodiments, the bandage is a fingertip bandage about 51 mm long and about 45 mm wide. In various embodiments, the bandage is a plastic bandage, a fabric bandage, a metal detectable bandage, or a combination thereof. In some embodiments, the bandage is medicated. In other embodiments, the bandage is non-medicated.

In another aspect, disclosed herein is a container, the container having about 5 to about 100 of the bandage application systems disposed therein. In some embodiments, the container has about 20 of the bandage application systems disposed therein.

In another aspect, disclosed herein are bandage application systems comprising: an individual sterile adhesive bandage; a first wrapper element; and a second wrapper element; the first and second wrapper elements each comprising two parallel sheets sealed on three of four sides to form a pocket, the first wrapper element and the second wrapper element at least partially enclosing the bandage in respective pockets, and the first wrapper element and the second wrapper element separably in contact to completely enclose the bandage. In some embodiments, the first and second wrapper elements are each printed to indicate an appropriate grip area. In some embodiments, the first and second wrapper elements are printed with bandage application instructions. In some embodiments, the first and second wrapper elements are separably in contact via a perforated, scored, or overlapping region. In some embodiments, upon separation of the first and second wrapper elements, the partially exposed bandage remains associated with either the first or the second wrapper element. In some embodiments, separation of the first and second wrapper elements does not require ripping or tearing of either the first or the second wrapper element. In some embodiments, the bandage is a strip bandage about 76 mm long and about 25 mm wide. In some embodiments, the bandage is a strip bandage about 76 mm long and about 19 mm wide. In some embodiments, the bandage is a strip bandage about 40 mm long and about 10 mm wide. In some embodiments, the bandage is a knuckle bandage about 76 mm long and about 38 mm wide. In some embodiments, the bandage is a fingertip bandage about 51 mm long and about 45 mm wide. In various embodiments, the bandage is a plastic bandage, a fabric bandage, a metal detectable bandage, or a combination thereof. In some embodiments, the bandage is medicated. In other embodiments, the bandage is non-medicated. In some embodiments, when the first and second wrapper elements are pulled in opposite directions the first and second elements separate to partially expose the bandage in a ready-to-apply state. In further embodiments, the bandage, when in a ready-to-apply state, is characterized by having at least one exposed adhesive area in a condition to adhere to skin. In some embodiments, the bandage comprises: a backing; at least one absorbent region; at least one adhesive region, wherein adhesive is applied to the backing; and a protection paper overlaying each adhesive region. In still further embodiments, upon separation of the first and second wrapper elements, at least one protection paper remains associated with a wrapper element, thereby exposing the adhesive.

In another aspect, disclosed herein are individual wrappers for an adhesive bandage, the wrapper comprising: a first wrapper element; and a second wrapper element; the first and second wrapper elements each comprising two parallel sheets sealed on three of four sides, the first and second wrapper elements separably in contact to form an interior adapted to completely enclose an individual adhesive bandage; provided that when the first and second wrapper elements are gripped and pulled in opposite directions the first and second elements separate to partially expose a bandage disposed in the interior in a ready-to-apply state. In some embodiments, the first and second wrapper elements are each printed to indicate an appropriate grip area. In some embodiments, the first and second wrapper elements are printed with bandage application instructions. In some embodiments, the first and second wrapper elements are separably in contact via a perforated, scored, or overlapping region. In some embodiments, upon separation of the first and second wrapper elements, a partially exposed bandage remains associated with either the first or the second wrapper element. In some embodiments, separation of the first and second wrapper elements does not require ripping or tearing of either the first or the second wrapper element. In some embodiments, the individual adhesive bandage comprises at least one adhesive region and a protection paper overlaying each adhesive region; wherein upon separation of the first and second wrapper elements, the at least one protection paper remains associated with either the first or the second wrapper element, thereby exposing the adhesive.

DETAILED DESCRIPTION OF THE INVENTION

Figure 1:
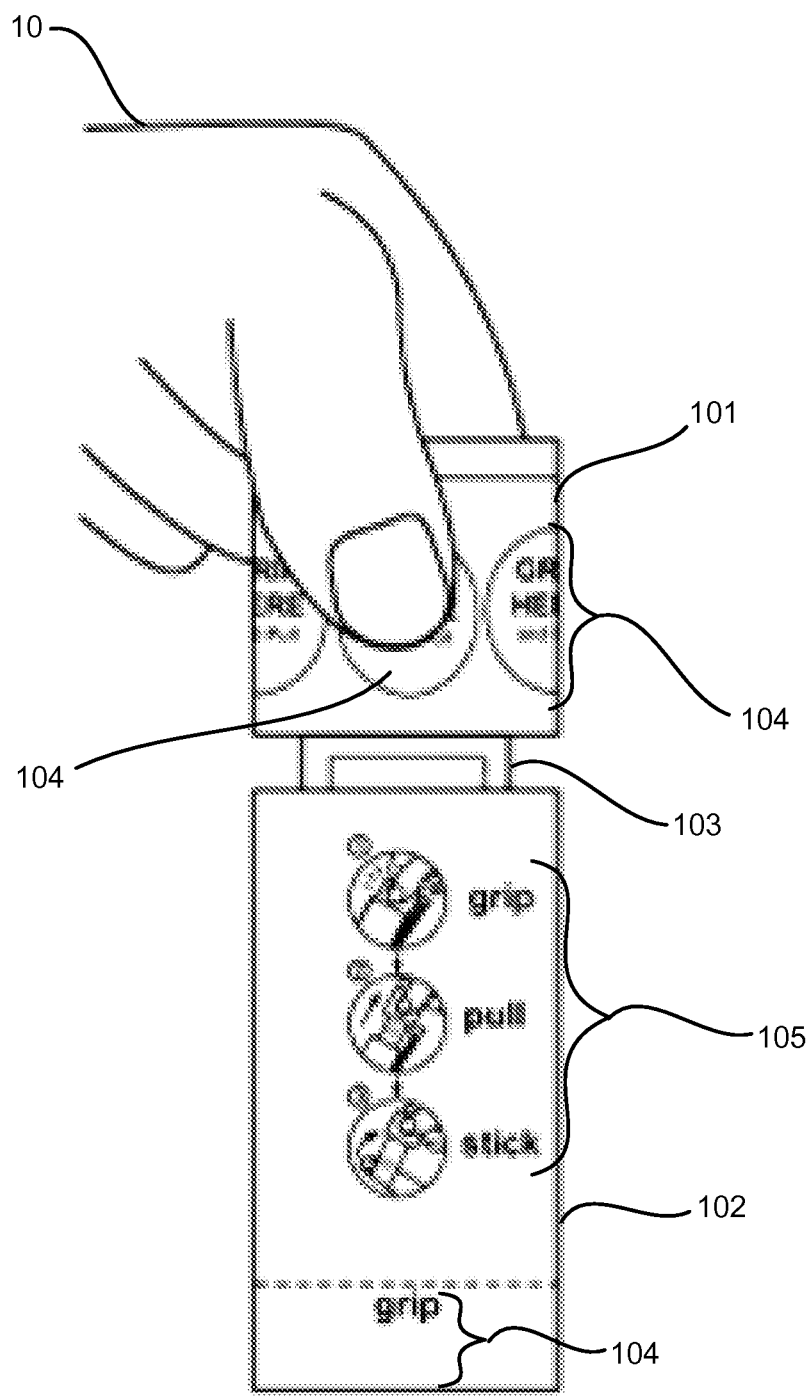
FIG. 1 illustrates a non-limiting example of a bandage application system; in this case, a system including an individual sterile adhesive bandage, a first wrapper element, and a second wrapper element. In this example, the two wrapper elements are slightly separated to reveal the bandage.

Described herein are bandage application systems, individual bandages, and bandage wrappers that allow efficient removal of the bandage from its packaging in a ready-to-apply state, which facilitates rapid application of the bandage and lowers the risk of the bandage becoming contaminated through excessive handling. In some embodiments, the bandage application systems, individual bandages, and bandage wrappers described herein allow for rapid removal of the bandage wrapper with only one hand and thus reduce the potential for user introduced bacteria and secondary infection.

Described herein, in certain embodiments, are bandage application systems comprising: an individual sterile adhesive bandage; a first wrapper element; and a second wrapper element; whereby the first wrapper element and the second wrapper element at least partially enclose the bandage and are separably in contact to completely enclose the bandage such that when the first and second wrapper elements are pulled in opposite directions the first and second elements separate to partially expose the bandage in a ready-to-apply state.

Also described herein, in certain embodiments, are bandage application systems consisting essentially of: an individual sterile adhesive bandage; a first wrapper element; and a second wrapper element; whereby the first wrapper element and the second wrapper element at least partially enclose the bandage and are separably in contact to completely enclose the bandage such that when the first and second wrapper elements are pulled in opposite directions the first and second elements separate to partially expose the bandage in a ready-to-apply state.

Also described herein, in certain embodiments, are bandage application systems comprising: an individual sterile adhesive bandage; a first wrapper element; and a second wrapper element; the first and second wrapper elements each comprising two parallel sheets sealed on three of four sides to form a pocket, the first wrapper element and the second wrapper element at least partially enclosing the bandage in respective pockets, and the first wrapper element and the second wrapper element separably in contact to completely enclose the bandage.

Also described herein, in certain embodiments, are bandage application systems consisting essentially of: an individual sterile adhesive bandage; a first wrapper element; and a second wrapper element; the first and second wrapper elements each comprising two parallel sheets sealed on three of four sides to form a pocket, the first wrapper element and the second wrapper element at least partially enclosing the bandage in respective pockets, and the first wrapper element and the second wrapper element separably in contact to completely enclose the bandage.

Also described herein, in certain embodiments, are individual wrappers for an adhesive bandage, the wrapper comprising: a first wrapper element; and a second wrapper element; the first and second wrapper elements each comprising two parallel sheets sealed on three of four sides, the first and second wrapper elements separably in contact to form an interior adapted to completely enclose an individual adhesive bandage; provided that when the first and second wrapper elements are gripped and pulled in opposite directions the first and second elements separate to partially expose a bandage disposed in the interior in a ready-to-apply state.

Also described herein, in certain embodiments, are individual wrappers for an adhesive bandage, the wrapper consisting essentially of: a first wrapper element; and a second wrapper element; the first and second wrapper elements each comprising two parallel sheets sealed on three of four sides, the first and second wrapper elements separably in contact to form an interior adapted to completely enclose an individual adhesive bandage; provided that when the first and second wrapper elements are gripped and pulled in opposite directions the first and second elements separate to partially expose a bandage disposed in the interior in a ready-to-apply state.

Certain Definitions

Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise. Any reference to "or" herein is intended to encompass "and/or" unless otherwise stated.

Adhesive Bandage

In some embodiments, the systems, packaging, and wrappers described herein include an adhesive bandage. Many types of adhesive bandages are suitable. In various embodiments suitable adhesive bandages include, by way of non-limiting examples, strip bandages, winged bandages, knuckle bandages, fingertip bandages, and the like. Many materials are suitable for an adhesive bandage described herein. In various embodiments, suitable adhesive bandages include, by way of non-limiting examples, plastic bandages, fabric bandages, metal detectable bandages, and combinations thereof. In some embodiments, an adhesive bandage is a non-medicated bandage. In other embodiments, an adhesive bandage is a medicated bandage. In some embodiments, an adhesive bandage is a sterile bandage.

In light of the materials and features described herein, those skilled in the art will recognize that a suitable adhesive bandage is somewhat elastic, flexible, durable, and water-resistant. In some embodiments, an adhesive bandage comprises a backing coated on one side with an adhesive. In some embodiments, a backing is coated on one side with an adhesive to define one adhesive region. In other embodiments, a backing is coated on one side with an adhesive to define a plurality of adhesive regions. In various further embodiments, a backing is coated on one side with an adhesive to define 2, 3, 4, 5, 6, or more adhesive regions. In some embodiments, an adhesive is further suitable for retaining an absorbent pad on the adhesive backing. In further embodiments, the adhesive is pressure sensitive, colorless, and transparent. In some embodiments, an adhesive bandage connects adhesively and reversibly to the skin. In some embodiments, an adhesive bandage described herein includes one or more protective papers overlaying the adhesive region or regions. In further embodiments, a protective paper temporarily overlays an adhesive region to preserve the adhesive region until the time of use. Many materials capable of easy release from the adhesive are suitable for protective papers including, by way of non-limiting examples, plastic and wax paper.

Many sizes are suitable for an adhesive bandage described herein. In some embodiments, an adhesive bandage described herein is about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more millimeters long or wide, including increments therein. In some embodiments, an adhesive bandage described herein is about 1, 2, 3, 4, 5, 6, 7, 8, 9, 10, 11, 12, 13, 14, 15, 16, 17, 18, 19, 20, or more centimeters long or wide, including increments therein. In particular embodiments, the adhesive bandages are of the dimensions of 10.2 cm long and 6.4 cm wide; 7.6 cm long and 2.5 cm wide, 7.6 cm long and 1.9 cm wide, 5.7 cm long and 1.5 cm wide and 2.2 cm long and 2.2 cm wide. In further embodiments, suitable shapes for an adhesive bandage include square and rectangular shaped bandages. In light of the dimensions and features described herein, those skilled in the art will recognize that suitable dimensions include those adapted to facilitate protection, facilitate healing, and lower the risk of infection for of a cut, scrape, puncture, or other wound or lesion, on any part of the human body.

Figure 4:
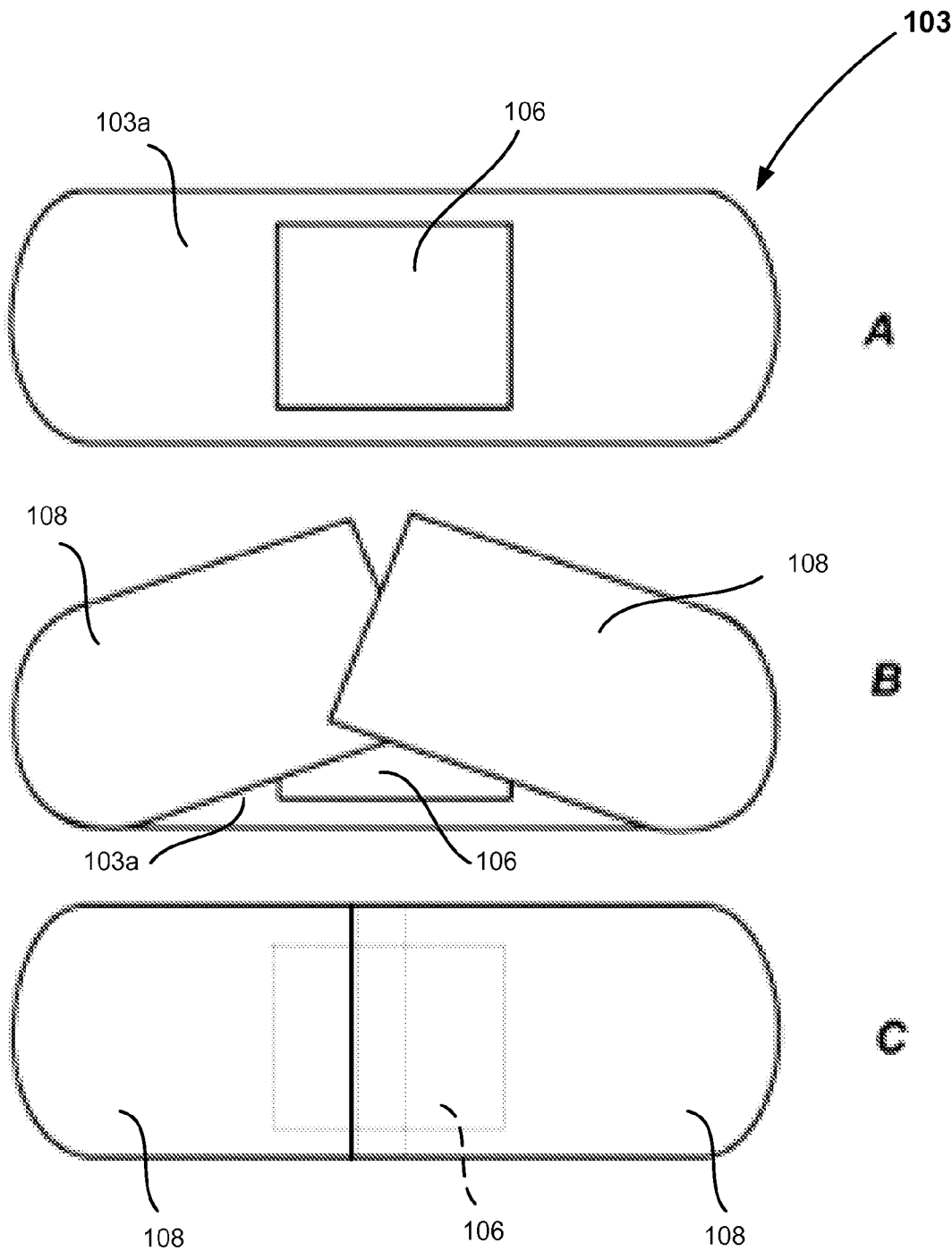
FIG. 4 illustrates a non-limiting example of an adhesive bandage; in this case, an adhesive bandage including a backing, an absorbent patch, and two adhesive regions. In this example, protective papers are depicted overlaying each adhesive region (C), partially removed from the adhesive regions (B), and completely removed (A).

Referring to FIG. 4, in a particular embodiment, an adhesive bandage 103 has been separated from wrapper elements but still includes protection papers 108 overlaying adhesive regions 103a. FIG. 4A displays the back of an adhesive bandage 103, opposite from a non adhesive region (103b, see FIG. 2) and an absorbent pad 106. FIG. 4B demonstrates partial removal of protection papers 108 overlaying adhesive regions 103a of the adhesive bandage, partially exposing the adhesive regions 103a as well as the absorbent pad 106. FIG. 4C demonstrates an adhesive bandage with the protection papers 108 completely overlaying adhesive regions and covering the absorbent pad 106.

Wrapper Elements

In some embodiments, the systems, packaging, and wrappers described herein include a first wrapper element and a second wrapper element. Many materials are suitable for first and second wrapper elements described herein. In various embodiments, suitable materials for the wrappers include paper, cardstock, plastic, and the like. In further embodiments, suitable materials for the wrappers include materials adapted for containing non-medicated bandages, medicated bandages, sterile bandages, strip bandages, winged bandages, knuckle bandages, fingertip bandages, plastic bandages, fabric bandages, metal detectable bandages, or combinations thereof. In light of the materials described herein, those skilled in the art will recognize that suitable materials are flexible, disposable, and capable of completely enveloping an adhesive bandage, capable of keeping the bandage clean and sterile, suitable for attachment on the interior of the wrapper elements to a protection paper overlaying an adhesive region of the bandage, and suitable for printing instructions on the exterior.

In some embodiments, the two wrapper elements each consist of two parallel sheets of material sealed on three of four sides with adhesive (or other method of bonding) to create a pocket used to contain an adhesive bandage. In further embodiments, each wrapper element contains one end of the bandage. In still further embodiments, two wrapper elements, each containing one end of the bandage, completely contain the bandage. In some embodiments, the two wrapper elements are separably in contact with one another while completely enveloping an adhesive bandage. In some embodiments, the first and second wrapper elements are the same size and each contain half of an adhesive bandage. In other embodiments, the first and second wrapper elements are different sizes and contain unequal portions of an adhesive bandage.

In some embodiments, the wrapper elements each partially enclose a portion of the adhesive bandage so that when they are separably in contact with one another the entire adhesive bandage is covered and enveloped. In further embodiments, when one element is separated from the other by pulling in opposite directions parallel to the orientation of the bandage, one of the wrapper elements remains associated with the adhesive bandage to facilitate application to the desired area and minimize handing of the bandage prior to application, and the other wrapper element dissociates from the bandage to expose the bandage in a ready-to-apply state.

Figure 2:
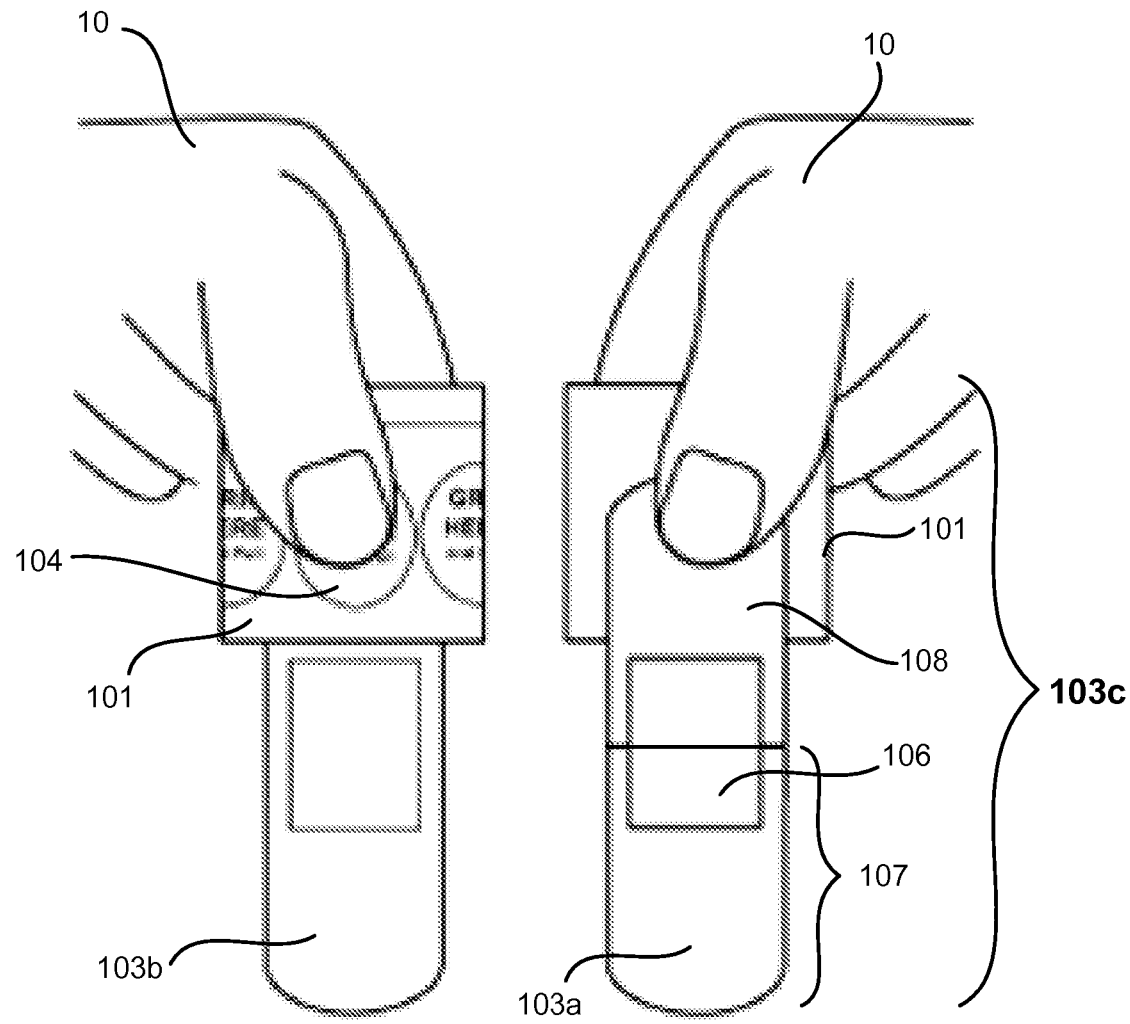
FIG. 2 illustrates a non-limiting example of a partially exposed adhesive bandage separated from one of the wrapper elements and in a ready-to-apply state; in this case, a partially exposed adhesive bandage including at least one exposed adhesive area in a condition to adhere to skin and one of the wrapper element still associated with the protective paper still overlaying an unexposed adhesive region on the bandage.

Referring to FIG. 2, in a particular embodiment, one of the wrapper elements 101 remains associated with an adhesive bandage along with a protection paper 108 overlaying a portion of an adhesive region 103a to facilitate handling of the adhesive bandage. In this particular embodiment, users 10 optionally handle the bandage in a ready-to-apply state 103c after exposing part of the adhesive region 107 by the removal of a wrapper element.

In some embodiments, one or more wrapper elements is attached to one or more protection papers such that dissociation of the wrapper element from the bandage removes the one or more protection papers thus exposing one or more adhesive regions. Many methods are suitable for attachment of a wrapper element and a protection paper. In various embodiments, suitable methods include application of adhesive, use of a fastener, and the like.

Figure 5:
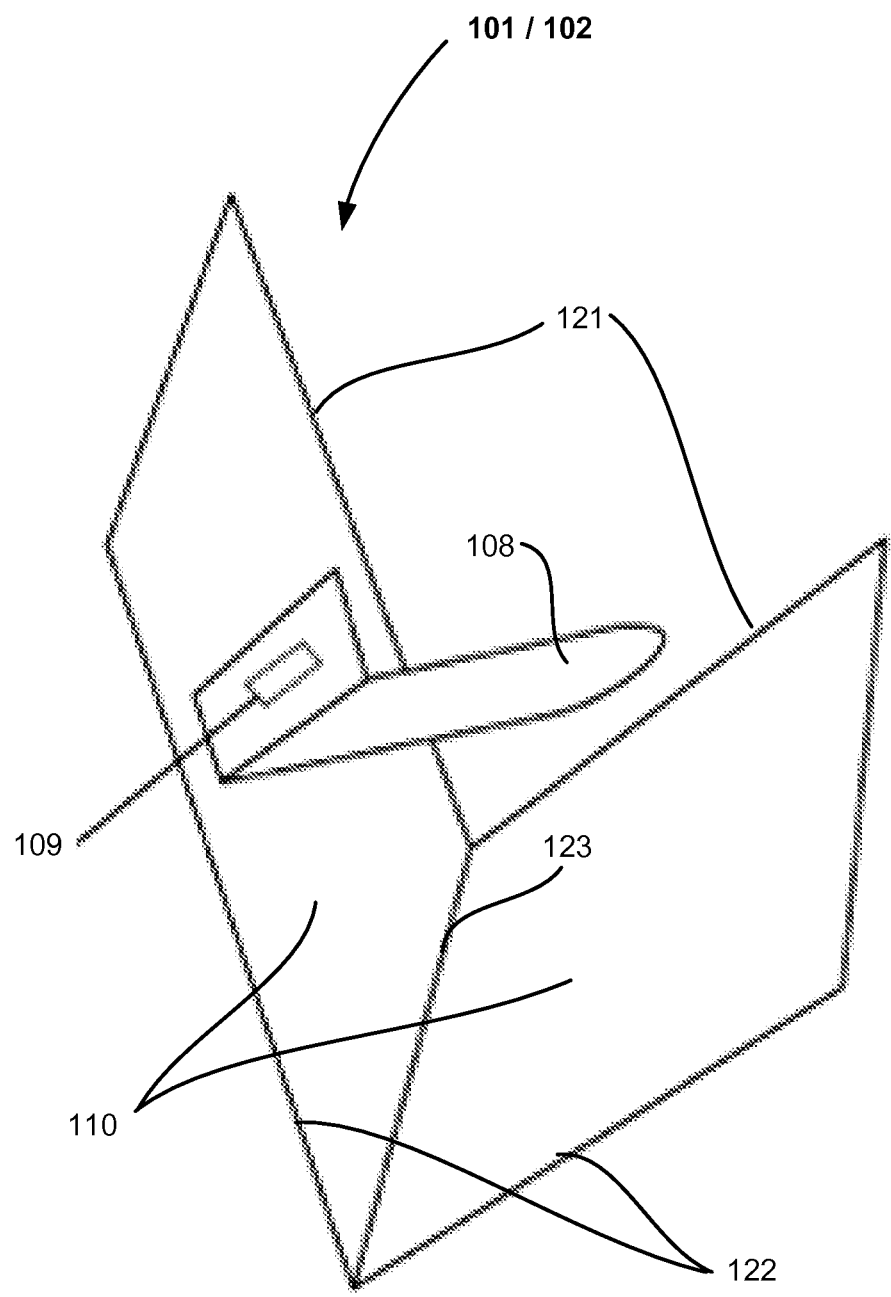
FIG. 5 illustrates a non-limiting example of a wrapper element associated with a protection paper after separation from the other wrapper element; in this case, the wrapper element is exploded to depict the wrapper element glued to the protection paper.

Referring to FIG. 5, in a particular embodiment, a wrapper element 101/102 includes glue 109 applied to connect to a protection paper overlaying an adhesive region on the bandage so that upon removal of the wrapper element 101/102, the protection paper 108 overlaying the adhesive region is removed as well.

In some embodiments, the first and second wrapper element, when separably in contact with each other, completely enclose an adhesive bandage. In some embodiments, the first and second wrapper elements are separably in contact with each other without being connected or consisting of one single wrapper. In further embodiments, the first and second wrapper elements are separably in contact via a perforated, scored, or overlapping region. In some embodiments, the first and second wrapper elements are easily and efficiently separated from each other while still completely enclosing the adhesive bandage when in contact with one another. In further embodiments, the first and second wrappers are separable while allowing the adhesive bandage to remain associated with one of the wrapper elements rendering the bandage ready-to-apply. In light of the described separable connection between wrapper elements, those skilled in the art will utilize methods of keeping wrapper element in contact to envelope the adhesive bandage without the elements being fully connected or the elements being rendered one single wrapper.

Referring to FIG. 1, in a particular embodiment, the wrapper elements 101,102 are separated from one another without the need to rip or tear the wrapper elements. This particular embodiment demonstrates two wrapper elements forming two separate pockets (110, see FIG. 5) sealed along three (121, 122, 123, see FIG. 5) of four sides that together completely envelope the adhesive bandage 103 and are separably in contact to facilitate efficient separation when needed for use. The embodiment of FIG. 1 also demonstrates printing 105 designating the appropriate grip areas 104 for proper removal of the wrapper elements in order to access the adhesive bandage 103.

In some embodiments, instructions are printed directly on the individual wrapper elements which eliminates the need for printed instructions on the container and eliminates the need for a dispenser to assist consumers. Many modes of communication are suitable for the instructions. In various embodiments, printed instructions communicated via words, symbols, pictograms, and combinations thereof. In further embodiments, instructions printed on the individually packaged bandages allows unfamiliar users to follow simple instructions printed on the individual packaging to access a bandage easily without needing to refer back instructions printed on a dispenser or container.

Figure 6:
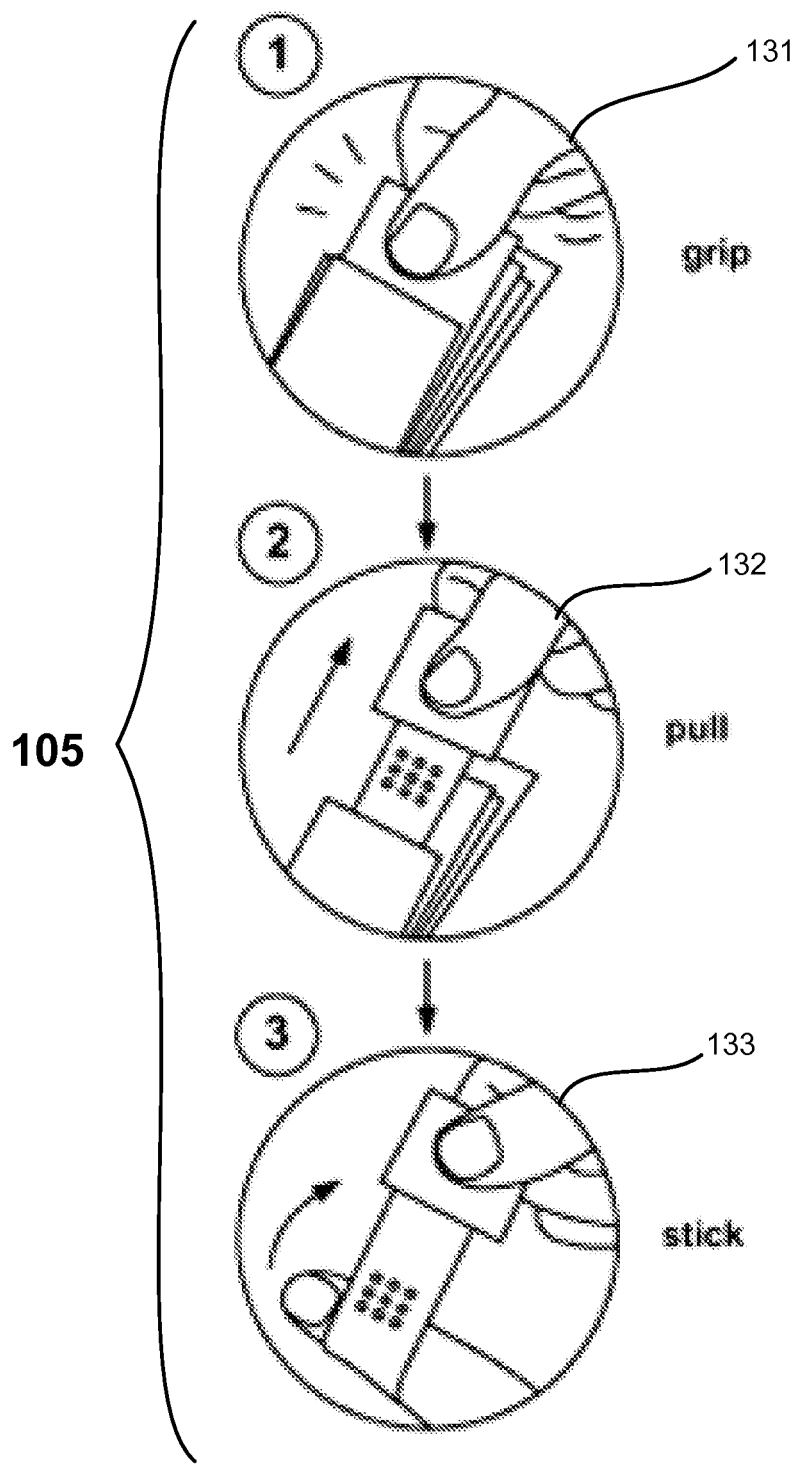
FIG. 6 illustrates a non-limiting example of printing to depict application instructions on a wrapper element; in this case, application instructions including directions (in words and pictograms) for how to efficiently separate wrapper elements to partially expose the adhesive region of a bandage to place the bandage into a ready-to-apply state and how to apply a ready-to-apply bandage to an area in need thereof using only one hand.

Referring to FIG. 6, this particular embodiment demonstrates the simple and easy to understand instruction 105 printed outside of the wrapper elements. In combination with the printed markings designating the appropriate grip areas (104, see FIG. 1), such instructions allow users to efficiently and rapidly deploy (131, 132) and apply (133) the adhesive bandage without the assistance of a dispenser apparatus.

Operation of the System

In some embodiments, a bandage in a ready-to-apply state includes one or more exposed adhesive regions, an exposed sterile absorbent pad, and an unexposed handling area crated by a wrapper element associated with the bandage. In some embodiments, an adhesive bandage described herein is rendered into a ready-to-apply state by a consumer pulling two wrapper elements in opposite directions parallel to the bandage. In further embodiments, pulling two wrapper elements in opposite directions parallel to the bandage separates the wrapper elements and partially exposes the adhesive bandage. In some embodiments, removal of a wrapper element exposes a portion of an adhesive region of the bandage, making it ready-to-apply to skin. In some cases, because a protection paper overlaying an adhesive region of the bandage is connected to a wrapper element, removal of one of the wrapper elements also removes the protection paper allowing the bandage to be applied onto the desired area without further handling (e.g., ready-to-apply). In a particular embodiment, an adhesive bandage is contained and oriented within two wrapper elements such that when one of the wrapper elements is removed, a portion of the bandage remains contained within one wrapper element and the remainder of the bandage is revealed, with an adhesive region exposed, ready to be applied onto the desired area.

In some embodiments, upon separation of the wrapper elements and removal of one of two wrapper elements, a bandage in a ready-to-apply state is rendered about 25, 30, 35, 40, 45, 50, 55, 60, 65, 70, 75, or 80 percent exposed, including increments therein. In further embodiments, upon separation of the wrapper elements and removal of one of two wrapper elements, a bandage in a ready-to-apply state remains about 25, 30, 35, 40, 45, 50, 55, 60, 65, 70, 75, or 80 percent contained within the remaining wrapper element, including increments therein.

Figure 3:
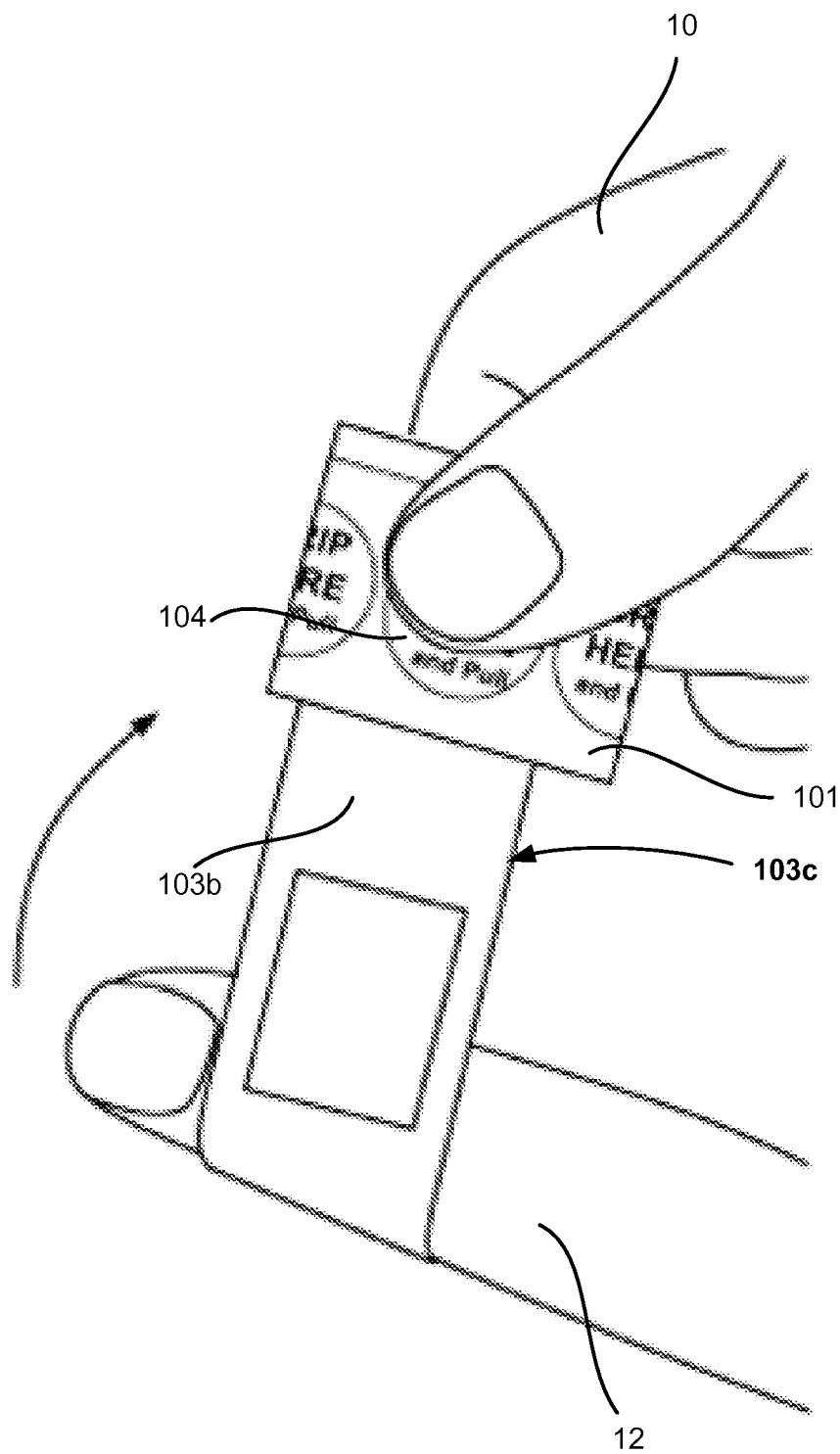
FIG. 3 illustrates a non-limiting example of a partially exposed adhesive bandage separated from one of the wrapper elements and in a ready-to-apply state; in this case, a partially exposed adhesive bandage including a partially exposed adhesive bandage with the exposed adhesive area applied to a finger while still associated with the remaining wrapper element.

Referring to FIG. 3, in a particular embodiment, an adhesive bandage remains associated with one wrapper element 101 and is in a ready-to-apply state (103c, see FIG. 2). This particular embodiment demonstrates the efficient application of an adhesive bandage onto a finger 12 while in a ready-to-apply state.

In some embodiments, an adhesive bandage is situated within the wrapper elements so that when a consumer grips appropriate areas indicated by printing on the wrapper elements, only one end of the bandage will be gripped along with one of the wrapper elements while the other wrapper element is free to be disassociated from the bandage. In further embodiments, an adhesive bandage is situated so that only one end does not extend into a printed grip area of a wrapper element so that during separation of the wrapper elements the user is only gripping a wrapper element without the bandage. In light of the described method of gripping and situating the adhesive bandage within the system, those skilled in the art will recognize orientations of the grip placement and the adhesive bandage within wrapper element(s) that allow the gripping of only one end of the bandage during separation of the wrapper elements.

In some embodiments, an adhesive bandage is situated within wrapper elements having instructions for application that are easily and readily understandable. In further embodiments, an adhesive bandage is situated within the wrapper elements which are printed with graphical and text-based instructions depicting steps necessary to grip both wrapper elements while gripping only one end of the adhesive bandage contained within, partially expose the bandage in a ready-to-apply state, and apply the partially exposed bandage. In light of the described instructions on the wrapper elements, those skilled the art will use instructions that explain how to remove wrapper elements and expose the adhesive bandage in a ready-to-apply state. In certain embodiments, instructions printed on the wrapper elements reduces or eliminates the need for a dispenser unit to allow rapid and sterile application of a ready-to-apply adhesive bandage.

Container

In some embodiments, a plurality of the bandage application systems described herein are disposed in a container that defines an interior compartment. In further embodiments, the bandage application systems are not connected or attached to each other or to the container (e.g., stored loose in a container), which is a substantial departure from traditional bandage dispensers. In still further embodiments, a container serves to preserve the packaged adhesive bandages from the outside environment and maintain the bandages in an efficient and organized manner so that bandages are easily transported, accessed, and utilized. Many types of containers are suitable. In various embodiments, suitable containers include both soft and hard boxes, bags, cartons, and envelopes. A suitable container is made of a wide array of materials. In various embodiments, a container described herein is made of cardstock, cardboard, fiberboard, plastic, nylon, and the like. In light of the disclosure provided herein, a skilled artisan will recognize that suitable materials are sturdy, somewhat rigid, water resistant, and inexpensive. In certain embodiments, a suitable container is shaped and sized to accommodate the type and number of bandages disposed in the interior.

A container described herein suitably includes a wide range of numbers of bandage application systems. In various embodiments, a container includes about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, or more individual bandage application systems, including increments therein. In various embodiments, a container includes at least 2, at least 5, at least 10, at least 15, at least 20, at least 30, at least 40, at least 50, at least 60, at least 70, at least 80, at least 90, at least 100, at least 200, at least 300, at least 400, or at least 500 individual bandage application systems, including increments therein. In various embodiments, a container includes about 2 to about 10, about 10 to about 20, about 20 to about 30, about 30 to about 40, about 40 to about 50, about 50 to about 60, about 60 to about 70, about 70 to about 80, about 80 to about 90, or about 90 to about 100 individual bandage application systems, including increments therein.

In some embodiments, the container includes multiple individually packaged bandages of the same dimension and type. In other embodiments, the container includes multiple individually packaged bandages of different dimensions and types. In further embodiments, the container includes a variety of bandages. In various embodiments, a container includes about 1, 2, 3, 4, 5, 6, 7, 8, 9, 10, 11, 12, 13, 14, 15, 16, 17, 18, 19, 20, or more types and/or sizes of individual bandage application systems.

EXAMPLE

The following illustrative example is representative of particular embodiments of the inventions described herein and not meant to be limiting in any way.

A consumer cuts his finger with a sharp knife while chopping vegetables in his kitchen. Knowing that rapid application of a sterile bandage can help to stop bleeding and prevent secondary infection, he immediately reaches for a container of 20 individual bandage application systems described herein. Each bandage application system includes a strip adhesive bandage. The bandage is made of a strip of fabric backing material, which is coated on one side with a transparent adhesive. To the adhesive is applied a sterile absorbent pad designed to contact a wound. The adhesive of the bandage is overlayed and covered by two plastic protection papers that reversibly adhere to the adhesive. Each bandage application system also includes two wrapper elements. Each wrapper element is made of two flat sheets of water resistant paper, which are sealed along three of four sides to form an envelope shaped pocket. Each pocket formed by a wrapper element is disposed over an end of the strip bandage. The two wrapper elements are further disposed to separably contact each other and fully contain the strip adhesive bandage. One of two plastic protection papers is glued to an associated wrapper element such that removal of the wrapper element from the bandage causes the protection paper to be removed from the adhesive of the bandage.

The individual bandage application system is thus situated such that gripping each of the two wrapper elements and pulling them in opposite directions separates the wrapper elements, without ripping or tearing the wrappers to partially reveal the bandage, with an adhesive area and the absorbent pad exposed, in a ready-to-apply state.

The consumer quickly scans the bandage application system and recognizes graphical and text instructions for application of the bandage printed on the outside of the wrapper formed by the two wrapper elements as well as printed grip areas (one on each wrapper element). The instructions depict three steps for application. The first step is to grip the bandage application system at the two grip regions indicated. The second step is to pull the two wrapper elements in opposition directions separating them to expose half of the bandage in a ready-to-apply state. The final and third step is to apply the bandage to cover and protect a wound.

Within a few seconds, the consumer has followed the application instructions to grip, pull, and apply the bandage. He successfully applies the bandage in a sterile fashion with one hand and without the aid of a dispenser device.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

What is claimed is:

1. A bandage application system comprising:
   a. an individual sterile adhesive bandage comprising
      i. a backing;
      ii. at least one absorbent patch;
      iii. two adhesive regions, wherein adhesive is applied to the backing, and each adhesive region having an overlaying protection paper;
   b. a first wrapper element; and
   c. a second wrapper element;
   whereby the first wrapper element and the second wrapper element at least partially enclose the bandage and are separably in contact to completely enclose the bandage such that when the first and second wrapper elements are pulled in opposite directions the first and second elements do not require ripping or tearing to separate to partially expose the bandage in a ready-to-apply state and said partially exposed bandage remains associated with one of the wrapper elements and the other wrapper elements dissociates from said bandage, and wherein only one of the two protection papers is attached to an associated wrapper element.

2. The system of claim 1, wherein the first and second wrapper elements each comprise two parallel sheets sealed on three of four sides.

3. The system of claim 1, wherein the bandage, when in a ready-to-apply state, is characterized by having at least one exposed adhesive area in a condition to adhere to skin.

4. The system of claim 1, wherein the first and second wrapper elements are each printed to indicate an appropriate grip area.

5. The system of claim 1, wherein the first and second wrapper elements are printed with bandage application instructions.

6. The system of claim 1, wherein the first and second wrapper elements are separably in contact via an overlapping region.

7. The system of claim 1, wherein the bandage is a strip bandage about 76 mm long and about 25 mm wide.

8. The system of claim 1, wherein the bandage is a strip bandage about 76 mm long and about 19 mm wide.

9. The system of claim 1, wherein the bandage is a strip bandage about 40 mm long and about 10 mm wide.

10. The system of claim 1, wherein the bandage is a knuckle bandage about 76 mm long and about 38 mm wide.

11. The system of claim 1, wherein the bandage is a fingertip bandage about 51 mm long and about 45 mm wide.

12. The system of claim 1, wherein the bandage is a plastic bandage, a fabric bandage, a metal detectable bandage, or a combination thereof.

13. The system of claim 1, wherein the bandage is medicated.

14. The system of claim 1, wherein the bandage is non-medicated.

15. A container, the container having about 5 to about 100 of the bandage application systems of claim 1 disposed therein.

16. A individual wrapper for an adhesive bandage, the wrapper comprising: a first wrapper element; and a second wrapper element; the first and second wrapper elements each comprising two parallel sheets sealed on three of four sides, the first and second wrapper elements separably in contact to form an interior adapted to completely enclose an individual adhesive bandage provided that when the first and second wrapper elements are gripped and pulled in opposite directions the first and second elements do not require ripping or tearing to separate to partially expose a bandage disposed in the interior in a ready-to-apply state and said partially exposed bandage remains associated with one of the wrapper elements and the other wrapper element dissociated from said bandage, wherein the bandage comprises a backing, at least one absorbent patch, two adhesive regions, wherein adhesive is applied to the backing, and each adhesive region having an overlaying protection paper, wherein only one of the two protection papers is attacked to an associated wrapper element.

17. The wrapper of claim 16, wherein the first and second wrapper elements are each printed to indicate an appropriate grip area.

18. The wrapper of claim 16, wherein the first and second wrapper elements are printed with bandage application instructions.

19. The wrapper of claim 16, wherein the first and second wrapper elements are separably in contact via an overlapping region.

* * * * *